United States Patent [19]

Serimian et al.

[11] Patent Number: Plant 6,543

[45] Date of Patent: Jan. 17, 1989

[54] NECTARINE TREE, "SUMMER LION"

[76] Inventors: Donald M. Serimian, 2961 McCall Ave.; Lionel M. Serimian, 11310 E. Manning, both of, Selma, Calif. 93662

[21] Appl. No.: 120,498

[22] Filed: Nov. 13, 1987

[51] Int. Cl.[4] ..... A01H 5/00

[52] U.S. Cl. ..... Plt./41

[58] Field of Search ..... Plt./41

*Primary Examiner*—Robert E. Bagwill

*Attorney, Agent, or Firm*—Worrel & Worrel

[57] ABSTRACT

A new and distinct variety of nectarine tree which is somewhat similar to the Red Lion Nectarine Tree (U.S. Plant Pat. No. 5,591) and the May Grand Nectarine Tree (U.S. Plant Pat. No. 2,794) with which it is most closely related but which is distinguished therefrom and characterized as to novelty by producing fruit which are mature for commercial harvesting approximately July 1 through July 12 in Fresno County, Calif. and which further produces fruit that exhibits a bright red skin color, a yellow colored, firm flesh and has excellent eating qualities.

1 Drawing Sheet

BACKGROUND OF THE NEW VARIETY

The present invention relates to a Nectarine Tree denominated varietally as "Summer Lion" and more particularly to such a nectarine tree which produces a clingstone fruit which has a very large size and a dark red skin color and which further is characterized as to novelty by producing a fruit which is ripe for commercial harvesting approximately July 1 through July 12 in the central portion of the San Joaquin Valley of central California.

From an economic perspective, the relative dates that various varieties of nectarine trees become ripe for commercial harvesting are of extreme importance. It has long been recognized as desirable to provide a nectarine tree which bears fruit during a portion of the season later than other varieties of nectarine trees with which it is most closely similar, whereby the fruit provided by same can be sent to market at a time when competition is at a minimum and the best price can be negotiated. Moreover, it has generally been agreed that an additional economic benefit can be attained if the harvesting period of a particular orchard is spread over a longer period of time because the capital expenditure attendant to harvest and transport of the fruit produced by the orchard can be spread over an extended period of time resulting in an overall lower cost of the final product and increasing the uniformity of production throughout an entire growing season.

The new and distinct variety of nectarine tree is characterized as to novelty by producing fruit which mature at mid-season, that is, approximately July 1 through July 12 in the central part of the San Joaquin Valley of central California, and in addition produces fruit having a large size, an attractive dark red skin color, and an excellent flavor.

ORIGIN AND ASEXUAL REPRODUCTION OF THE NEW VARIETY

In a continuing effort to upgrade the quality of their fruit, the applicants have routinely cross pollinated known varieties of nectarine trees having desirable characteristics and thereafter carefully studied the progeny produced from this procedure to determine if a new variety of nectarine tree was produced. The present variety of nectarine tree resulted from this course of conduct.

The new and distinct variety of nectarine tree hereof was the offspring produced from a successful cross pollination of a Red Lion variety of nectarine tree (U.S. Plant Pat. No. 5,591) and a May Grand Nectarine Tree (U.S. Plant Pat. No. 2,794); the cross pollination technique being performed by the inventors on the inventors' property located at 11024 East Dinuba Avenue in Selma, Calif. The first cross pollination, which occurred in 1983 produced offspring which were noted to have desirable characteristics. The inventors thereafter successfully asexually reproduced the new and distinct variety by budding it into test trees on the same property located in Selma, Calif. The first successful asexual reproduction took place in 1984. The progeny produced from these first asexual reproductions have been continually observed by the inventors and it has been subsequently determined that the progeny produced possess the same distinctive characteristics as the original offspring.

SUMMARY OF THE NEW VARIETY

The Summer Lion Nectarine Tree is characterized by many of the desirable features found in the Red Lion Nectarine Tree (U.S. Plant Pat. No. 5,591) and the May Grand Nectarine Tree (U.S. Plant Pat. No. 2,794), but has the important distinction of bearing fruit which is ripe for commercial harvesting approximately six weeks earlier than the Red Lion Nectarine Tree and approximately one month later than the May Grand Nectarine Tree, and which furthermore produces fruit having a large size and an intense red skin coloration, the variety furthermore being clingstone by nature.

BRIEF DESCRIPTION OF THE DRAWINGS

The accompanying drawing is a color photograph of three mature fruit of the subject variety, one of which has been divided in the axial plane to display the flesh coloration, and the other two displaying their external coloration sufficiently matured for harvesting and shipment, together with a twig bearing typical leaves which display the ventral and dorsal coloration thereof, along with two stones, all of the subject variety.

DETAILED DESCRIPTION

Referring more specifically to the pomological details of this new and distinct variety of nectarine tree, the following has been observed under the ecological conditions prevailing at the applicants' orchard which is located at 11024 East Dinuba Avenue, Selma, Calif. All major color code designations are by reference to the "Dictionary of Color" by Maerz and Paul, Second Edition, published in 1950, common color names are also used in several instances.

TREE

Size:
*Generally.*—average.
Vigor: Average; hardy when grown under normal San Joaquin Valley climatic conditions.
Figure: Upright and spreading. Tree form and density will be determined by pruning practices.
Trunk:
*Thickness.*—medium.
*Surface texture.*—average.
*Color of bark.*—gray-brown (7-C-9).
*Lenticels — generally.*—large, heavily calloused lenticels are present.
*Lenticels — numbers.*—numerous.
*Lenticels — color.*—medium brown, (14-H-11).
Branches:
*Size.*—average.
*Surface texture.*—medium.
*Color — mature branches.*—medium brown, (15-J-9).
*Lenticels — numbers.*—average.
*Color — immature shoots.*—light green, (20-H-4).
*Color — exposed young shoots.*—this part of the plant is often tinged with red.
*Texture.*—immature shoots — smooth.

LEAVES

Size:
*Generally.*—medium to large.
*Length.*—the average length is approximately 17.9 cm.
*Width.*—relatively narrow; the average width is approximately 4.6 cm.
Form:
*Generally.*—lanceolate with acuminate apex.
Color:
*Dorsal surface.*—medium green, (23-L-7).
*Ventral surface.*—gray-green, (21-J-5).
*Large leaf vein.*—light green-yellow, (18-J-2); the large leaf vein is approximately 1 mm. in thickness at mid vein.
Leaf margins:
*Form.*—finely crenate, the crenations are regular, and shallow. The leaf margins are moderately undulate.
Leaf petiole:
*Size.*—variable, medium to slightly short.
*Length.*—approximately 8 to 10 mm.
*Thickness.*—approximately 1½ to 2 mm.
*Color.*—a light gray-green, (18-H-2). The petiole groove is somewhat slightly darker in color, (19-I-5).
Leaf glands:
*Size.*—medium.
*Form.*—usually reniform.
*Numbers.*—generally two.
*Location.*—the two leaf glands are usually located on the petiole just below or on the basal leaf margin. One or more additional leaf glands may be located approximately 1 mm. up on the base of the leaf margin.
*Leaf gland pattern.*—variable, alternate to opposite.
*Color.*—a light shiny green, (18-K-3) when young. The gland color will darken and brown with advancing age.
Stipules:
*Numbers.*—two.
*Location.*—at the base of the leaf petiole.
*Length.*—approximately 7 to 9 mm.
*Color.*—light green, (18-J-6) when young. This color will darken and become brown with age. Early deciduous.
Flowers:
*Generally.*—the bloom of the subject variety was observed in the orchard of origin on Mar. 8, 1987.
*Blooming time.*—mid season to slightly late in relation to other common nectarine varieties growing in the central portion of the San Joaquin Valley of central California.
*Date of full bloom.*—Mar. 9, 1987.
*Flower size.*—generally — large and showy in form; approximately 42 to 48 mm. in diameter when fully expanded.
*Bloom amount.*—medium to slightly below average in density.
Flower buds and scales: The scales are pubescent and gray-brown in color, (15-C-5).
*Bud size.*—medium with respect to the species.
*Bud form.*—conic.
*Flower buds produced per node.*—generally one to two.
*Petals — size.*—large; length — approximately 23 to 24 mm.; width — approximately 17 to 18 mm.
*Petals — form.*—ovate.
*Claw.*—short; moderately broad; and truncate. The petals are cupped inwardly and the margins are undulate giving the flower an outwardly ruffled appearance.
*Petal color.*—light pink when young (1-E-2); a slightly darker color appears basally, (1-G-2). The petals darken with advancing age and assume a deep rose color (1-F-5), however the petal edges retain the original light pink color, (1-E-2).
*Pedicel — length.*—very short, approximately 1 mm. in length.
*Pedicel — thickness.*—approximately 1.5 mm.
*Pedicel — color.*—green (19-K-5).
*Nectaries.*—color — orange (11-J-11). This color darkens somewhat with advancing age.
*Anthers — size.*—small and shriveled in appearance.
*Anthers — color.*—light cream, (10-H-4).
*Pollen.*—generally — lacking. The variety appears to be pollen sterile or very nearly so.
*Stamens.*—length — approximately 10 to 13 mm. The length of the stamen is variable, but as a general matter it is usually shorter than the pistil.
*Stamens — color.*—light pink, (1-C-1). This color darkens with advancing maturity and later assumes a deep rose color, (1-E-5).
*Pistil — color.*—yellow-green, (17-H-3).

*Pistil — position.*—generally above the anthers when fully extended.

*Pistil — length.*—approximately 17 to 18 mm.

*Pistil — texture.*—glabrous.

FRUIT

Maturity when described: Ripe for commercial harvesting, approximately July 1 through July 12, 1987 in Fresno County, Calif.

Size:

*Generally.*—uniform, and very large.

*Average axial diameter.*—approximately 86 mm.

*Average cheek diameter.*—approximately 84 mm.

*Average suture diameter.*—approximately 85 mm.

Form:

*Generally.*—uniform, and slightly asymmetrical with one-half of the fruit being slightly larger than the other half.

*Form.*—ovate in the lateral aspect, nearly globose in the apical aspect.

Suture:

*Generally.*—the suture appears as a narrow line which extends from the base to the apex. The color of the suture line generally matches the color of the underlying blush or ground color of the fruit. The ventral suture line is moderately depressed; the depression is deepest in the stem cavity and a moderately deep depression occurs next to the apex on the ventral suture side. The suture depression is also visible, but not as deep, on the dorsal side of the fruit, this depression extending from the apex to the basal shoulder.

Ventral surface:

*Generally.*—rounded and moderately lipped; this trait is usually more noticeable on one side of the fruit.

Stem cavity:

*Generally.*—moderately deep.

*Form.*—narrowly oval.

*Average width.*—approximately 34 to 38 mm.

*Average length.*—approximately 37 to 43 mm.

*Average depth.*—approximately 16 to 19 mm. In those instances where the fruit was attached to the limb, an indentation may be evident.

Base:

*Form.*—slightly oblique to the fruit axis although occasionally it may appear at nearly right angles to the fruit axis.

Apex:

*Generally.*—low and rounded.

*Pistil point.*—oblique. Distinct depressions appear on both sides of the pistil point along the ventral and dorsal suture.

Stem:

*Length.*—the average length is approximately 8 to 12 mm.

*Thickness.*—the average thickness is approximately 4 to 4.5 mm.

*Color.*—light green-yellow, (17-J-4).

Skin:

*Thickness.*—average to above average.

*Flavor.*—mild.

*Tendency to crack.*—not observed.

*Tenacious to flesh.*—yes.

*Texture.*—glabrous.

Skin color: Variable; dark red to a lighter cherry-red, (7-L-9) through (5-L-10).

*Blush color.*—generally — the blush color covers approximately 85% to 95% of the fruit surface, and only a small amount of ground color is visible. If the ground color is visible, it will usually appear in the basal area. Some red colored streaks occasionally occur over the basal shoulder area. A small amount of speckling is evident. If present, the speckling is located over the apical shoulders.

*Ground color.*—yellow, (10-K-2).

Flesh color:

*Generally.*—at commercial maturity the flesh color is a bright amber-yellow (10-I-3). The flesh color is generally uniform from the skin to the pit cavity.

*Color.*—surface of pit cavity — stained red (5-K-9). This color extends approximately 2 to 3 mm. into the flesh. Some red flecking in the flesh is apparent with advancing maturity. This trait is illustrated in the drawings.

Flesh texture: Firm and crisp at commercial maturity; the subject variety softens and becomes juicy with advancing maturity.

Flesh fibers:

*Numbers.*—average.

*Length.*—medium.

*Texture.*—fine and tender.

Ripening: The subject variety ripens evenly.

Flavor: Rich, highly flavored.

Aroma: Slight.

Overall eating quality: Excellent.

STONE

Attachment: Full clingstone. The stone of the subject variety does not break free from the flesh.

Size:

*Generally.*—large.

*Length.*—approximately 42 to 44 mm.

*Width.*—approximately 29 to 31 mm.

*Breadth.*—approximately 22 to 23 mm.

Fibers:

*Numbers.*—numerous.

*Length.*—medium. The fibers of the subject variety show a strong attachment to the stone.

Form: Oval to very slightly obovate.

Base:

*Shape.*—truncate. The base is slightly oblique or at right angles with respect to the fruit axis.

Hilum:

*Generally.*—moderately large and heavily eroded.

*Form.*—a very narrow oval.

Apex:

*Shape.*—pointed, with a sharp acuminate tip.

Sides:

*Shape.*—variable, nearly equal, occasionally noticeably unequal.

Stone surface:

*Generally.*—very rough with coarse high prominent ridges disposed over the apical shoulders laterally, and large irregular pits are evident from the basal shoulders to mid-stone laterally.

Ventral edge:

*Generally.*—coarse, and moderately wide, with lateral ridges converging at the ventral edge. Occasionally a low wing occurs over the basal ventral suture area.

Dorsal edge:

*Form.*—substantially narrower than the ventral edge with high discontinuous ridges along the dorsal suture, and a moderately wide groove basally. The groove of the subject variety narrows over the apical shoulders. The apical shoulder is slightly eroded, this is particularly evident in the area from the apex to a position approximately to 7 to 8 mm. below the apex.

Stone color: Buff (10-E-3). The stone of the subject variety retains a slight maroon colored stain from the surrounding flesh fibers.

Tendency to split: An occasional split stone may be found; substantial numbers of split stones were not observed.

Use: Fresh market, for both long distance shipping and local use.

Resistance to disease: No particular susceptibilities noted.

Keeping quality: Good.

Shipping quality: As yet to be determined although the firm, crisp flesh exhibited by the fruit of the subject invention strongly indicates that the instant variety will have noteworthy shipping characteristics.

Although the new variety of nectarine tree possesses the desired characteristics as a result of the growing conditions prevailing in Fresno County, Calif., in the central part of the San Joaquin Valley, it is to be understood that variations in the usual magnitude and characteristics incident to growing conditions, fertilization, pruning and pest control are to be expected.

Having thus described and illustrated our new variety of nectarine tree, what is claimed as new and desired to be secured by Plant Letters Patent is:

1. A new and distinct variety of nectarine tree substantially as illustrated and described which is somewhat similar to the May Grand Nectarine Tree (U.S. Plant Pat. No. 2,794), and the Red Lion Nectarine Tree (U.S. Plant Pat. No. 5,591) from which it was derived as a cross pollinated seedling but from which it is distinguished therefrom and characterized as to novelty by producing fruit which are mature for commercial harvesting approximately July 1 through July 12 in the San Joaquin Valley of central California and which additionally produces fruit which have a very large size, a clingstone nature, a dark red skin color and a flesh color which is amber-yellow; the fruit of the subject variety having noteworthy eating qualities.

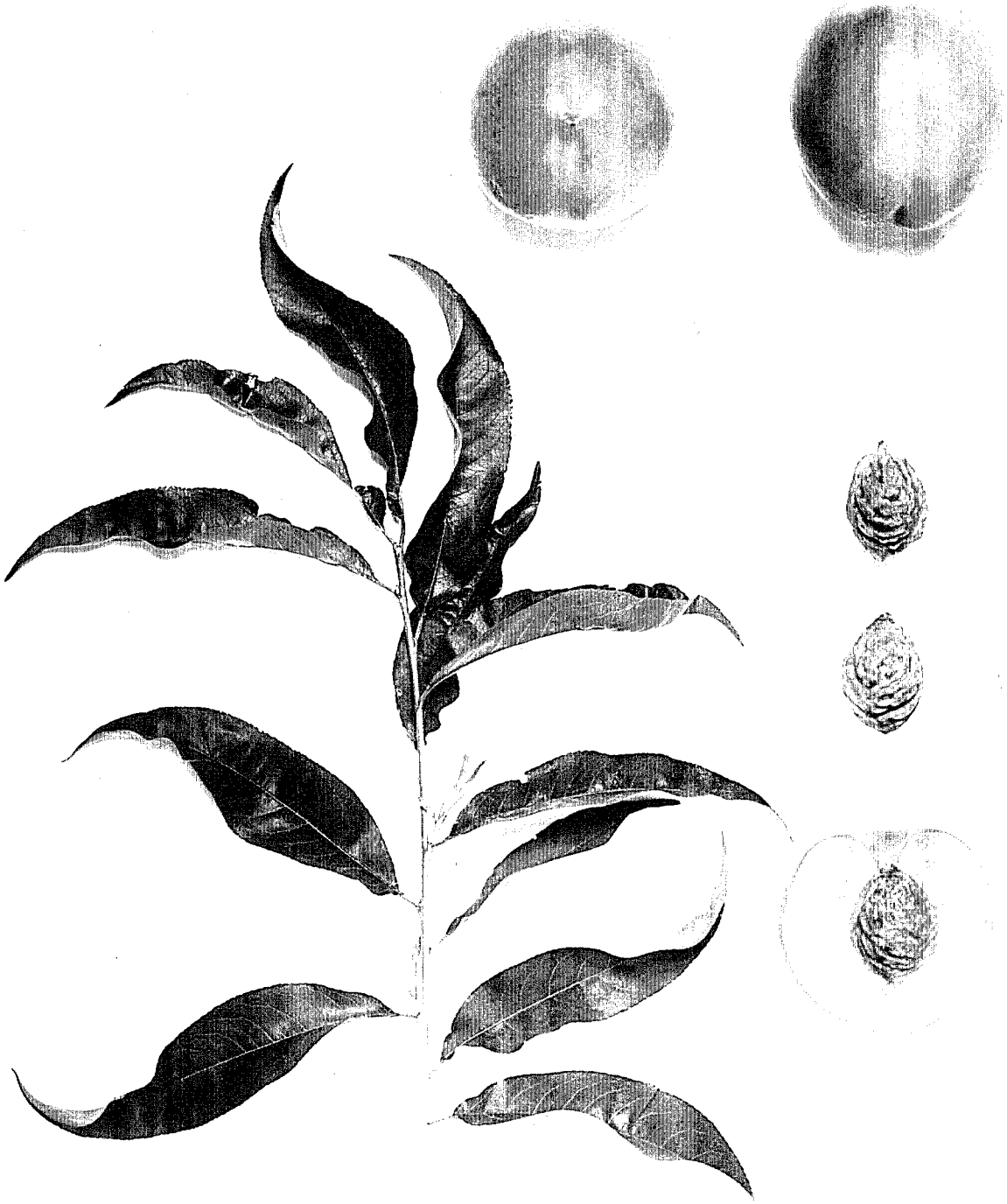

* * * * *